(12) United States Patent
Marcello

(10) Patent No.: US 6,951,662 B1
(45) Date of Patent: Oct. 4, 2005

(54) METHOD FOR PRODUCING A BIOLOGICAL SUBSTANCE, BIOLOGICAL SUBSTANCE AND THE USE THEREOF

(75) Inventor: Dell 'Eva Marcello, Esselbach (DE)

(73) Assignee: Gut zum Lebin Nahrungsmittel von feld und Hof GmbH, Marktheidenfeld-Altfeld (DE)

(*) Notice: Subject to any disclaimer, the term of this patent is extended or adjusted under 35 U.S.C. 154(b) by 0 days.

(21) Appl. No.: 09/762,347

(22) PCT Filed: Aug. 4, 1999

(86) PCT No.: PCT/DE99/02371

§ 371 (c)(1),
(2), (4) Date: Jul. 13, 2001

(87) PCT Pub. No.: WO00/08121

PCT Pub. Date: Feb. 17, 2000

(30) Foreign Application Priority Data

Aug. 4, 1998 (DE) .............................. 198 34 925

(51) Int. Cl.⁷ ................................................ A23L 1/36
(52) U.S. Cl. ..................... 426/629; 426/518; 426/519; 426/598; 426/601; 426/656
(58) Field of Search ................................ 426/598, 629, 426/601, 656, 518, 519

(56) References Cited

U.S. PATENT DOCUMENTS 3,697,290 A * 10/1972 Lynn ........................... 426/629
3,969,514 A    7/1976 Tiemstra
4,515,818 A    5/1985 MacDonald et al.
4,639,374 A    1/1987 Matsunobu et al.
5,667,838 A    9/1997 Wong et al.

FOREIGN PATENT DOCUMENTS

| EP | 0 475 510 A2 | 9/1991 | ............. A23D 9/00 |
| WO | WO 92/20243 | 11/1992 | ............. A23L 1/38 |
| WO | WO 96/19121 | 6/1996 | ............. A23L 1/38 |

OTHER PUBLICATIONS

IBi-Brotaufstriche, Internet, lebegesund.de Jan. 19, 2005.*
XP-002128686, 1 page, 1993.

* cited by examiner

*Primary Examiner*—Helen Pratt

(57) ABSTRACT

The invention relates to a method for the production of a substance, more particularly, a substance that can be used as foodstuff or cosmetic. Said substance is obtained from a first substance that is produced by fine grinding grains or nuts, especially sunflower seeds and by adding a first liquid and salt, sugar or substances similar to salt or sugar. By adding oil, especially sunflower seed oil, or a liquefied fat, a second liquid substance is normally obtained which acquires a more solid consistency by adding a second acid liquid or acidifying agent, especially lemon juice. The amount of the second acid liquid determines the consistency of the first substance. The invention is based on a basic substance for the production of foodstuff and cosmetic products exclusively consisting of a small number of original, natural, genetically unaltered substances that have not been genetically modified -nd that contain no additives or residues from drugs or hormones and ostensibly reduce allergens. The basic substance has optimal value as food stuff and can be used basically as a substitute for dairy products.

20 Claims, No Drawings

METHOD FOR PRODUCING A BIOLOGICAL SUBSTANCE, BIOLOGICAL SUBSTANCE AND THE USE THEREOF

This application is a 371 of PCT/DE99/02371 filed Aug. 8, 1999.

The invention relates according to claim 1 to a process for producing a substance which can serve the most varied purposes and is optimally suitable, in particular, for further processing as food and for further processing as toiletry or cleaning composition. In addition, the invention according to claims 10, 12 and 14 also comprises the foods, toiletries and cleaning compositions created by the process.

In particular in food production, differing biological and chemical substances are currently used. In many industrially packaged food end products, there is therefore a labelling requirement for the constituents in order to keep the consumer informed about their contents, and in particular to give people at risk of allergies the possibility of avoiding harmful substances.

In the case of other food end products, in particular those which are not industrially packaged, frequently the constituents are not completely identifiable for the consumer, however.

Modern food end products contain a multiplicity of base substances and additives which in most cases have passed through numerous processing steps and are far removed from the original natural foods. Despite the labelling obligation, consumers frequently cannot gain information about the substances listed on the labelling, which in turn are made up of substances subjected to numerous processing steps which are not labelled. This also applies, in particular, to preservatives and genetically engineered substances used which are occurring increasingly more widely and in an uncontrolled manner. Very disadvantageously, some economic plants, for example soya plants, can be obtained virtually only in genetically engineered form.

In addition, for historical reasons, in our developed region, numerous foods are produced using cowls milk, cow's milk products and chicken's eggs. Inter alia, in this context the disposition to allergic reactions to these foreign proteins of animal origin is known. Cow's milk products, even those organically produced, and chicken's eggs contain not inconsiderable residues of medicaments and hormones administered on an industrial scale to the animals, which are finally supplied to the end consumer. Other allergens occur due to animal feeds. In addition, cow's milk contains aluminium and lead, which is not safe even in small doses.

To provide foods, toiletries and cleaning compositions for people who have allergies and consumers who prefer drug-free and hormone-free foods, and also for vegetarians, it is necessary to replace the above-mentioned foreign protein products by a substance which is as natural as possible, passing through as few industrial processing steps as possible.

From the aspect of transparency of constituents of food end products for consumers, foods are advantageous which are fabricated from a small number of original and natural ingredients using as few industrial processing steps as possible.

The object therefore underlying the invention is to provide a base substance for the production of foods, toiletries and cleaning compositions, which base substance consists of original, natural substances which have not come into contact with genetic engineering.

The invention complies with these requirements to a great extent, its substances, furthermore, being able to be classified as vegan products.

The invention in addition complies with the object of providing a value-optimized food with very low pollution of the human body.

According to the invention, a first pulpy substance is produced from the fine comminution or wet milling of seeds or nuts with addition of a liquid and, in particular, of salt or sugar or other salt-like or sugar-like substances. This first substance, with addition of oil or liquefied fat, becomes an essentially liquid second substance, the latter gaining a more solid consistency by addition of an acidic liquid. In this case the amount of the acidic liquid determines the consistency of the substance finely produced. Consistency here shall be taken to mean either the viscosity of a liquid to pulpy mixture or the firmness of a glutinous to solid material composition.

The small number of base substances and constituents and the simple mechanical processing steps permit high levels of control and monitoring with respect to the end product. Residues of drugs and hormones and genetically engineered ingredients can be avoided reliably and the number of potential allergens can be markedly reduced.

The pulpy first substance consists of seeds, especially sunflower seeds, or nuts which are finely comminuted to form a homogeneous mixture, or are wet milled until essentially no grains are any longer present.

Equal quantities of the pulpy first substance are then cuttered (blended) with oil or liquefied fat, so that a second in most cases, viscous, substance is formed.

The oil introduced is preferably a vegetable oil and can, for example, be sunflower oil, olive oil or thistle oil. However, in a further alternative aspect, any other edible oil or fat whose flavour constituents or nutrients are desired in the substance produced according to the invention can also be used.

The quantitative ratios with respect to their contents by weight in the pulpy first substance can be as follows: seeds (or nuts) to liquid to salt or sugar etc.

100:50 to 1 000:0 to 200

Where below specific quantitative contents are used as a basis, these are specified on the basis of their contents by weight.

It has been found that the more of the first liquid was used, generally also the creamier the first pulpy substance became. However, a point can be reached at which, depending on the starting materials and the respective quantitative ratios, no liquid absorption takes place any longer and flocculation or persistence of undissolved liquid can occur.

The quantitative ratio of pulpy first substance to oil or liquefied fat can be about 100:20 to 300.

The substance finally produced, that is to say the subject-matter of the invention, is produced by blending the second substance with an acidic liquid. Acidic liquids which are highly suitable are acidulants, for example juices of the plant genus *Citrus*, that is to say lemon juice or lime juice, or natural acidification by bacteria.

However, other natural or semi-natural acidic liquids or acidulants, principally corresponding to the nature of the invention, can also be used. The quantitative ratio in the blending of the acidic second liquid to the liquid second substance can be about 2 to 20:100. The substance finally produced has a pH in the slightly acid range.

When the acidic second liquid or acidulant is added, a reaction takes place which leads to an altered viscosity, that is to say to a more solid substance. This reaction occurs, astonishingly, even when acidic liquid is added dropwise. This more solid substance can be whipped with air or nitrogen to a limited extent.

From the stage of the still pourable second substance, with increasing addition there proceeds the transition to the pasty, not yet solid state, having a consistency similar to curd cheese or fresh cheese and a lighter colour and creamy consistency.

A specific and preferred embodiment is described below.

100 grams of sunflower seeds are finely comminuted by cuttering or are wet milled until no grains are any longer present. The temperature during this comminution process is preferably about 20 degrees Celsius. A homogeneous mixture is produced into which 165 grams of water and 8 grams of salt are added, so that a stirrable, in particular pulpy, substance is formed. 200 grams of sunflower oil are cuttered into this pulpy substance. A light grey viscous mixture is formed.

The next working step provides the addition of 40 grams of fresh lemon juice. The viscous mixture reacts in this case to form a light pasty substance of similar consistency to curd cheese or fresh cheese, slightly raised by air whipped in during the mixing operation.

This substance has been found to be outstandingly suitable as substitute or base substance for essentially all solid and liquid foods in which milk products and milk protein products have previously been used, for example cream, curd cheese, cheese or the like.

This substance already represents a freely handleable independent base substance which can be supplied to varied applications.

If this substance is to be shelf-stable for a longer period, its pH can be set to preferably about 4.5 and/or pasteurization can be performed.

If the inventive substance is further processed, for example as drink, a content of a flavouring substance, for example in the form of fruit juice constituents, is suitable in order to provide a substitute for the customary flavoured milk drinks.

Depending on the seasoning of the substance produced, this can also be used, with appropriately adjusted firmness, as substitute for or additive to cheese, sausage or meat.

If sweet flavourings are added, patisserie products, for example cheesecakes or cream cakes or tartlets and the like can be produced. Yoghurt, curd cheese and fresh cheese products can also be produced with suitable adjustment of the viscosity by using the inventive substance.

Surprisingly, it has been found that toiletries having a very low content of allergens can also be prepared on the basis of the substance produced. Thus creams, sun-screen milks and the like can be prepared by addition of appropriate perfuming substances, preferably in the form of herb or plant constituents.

Cleaning compositions can also be prepared using the inventive substance, in which case these then also preferably have a grainy constituent.

The granular constituent can comprise coarsely ground sunflower seeds or sunflower seed meal, sawdust, grated coconut, sand or lime constituents and essentially serves an additional mechanical cleaning operation.

Although the invention has been described above with reference to preferred embodiments, it is not restricted to these.

For example, the sequence of the process steps can be altered or, in each case, instead of products of one variety, for example seeds or juices of only one plant or fruit variety, mixtures of seeds and juices of a plurality of plant or fruit varieties can be used. In addition, not only is pure replacement of milk protein products possible, but also addition to these or partial replacement.

However, in addition to milk protein products, for example, tofu-containing products and tofu itself can be replaced.

The amount of fat and fat properties (firmness of the fat) determine in general the consistency of the substance to the extent that consistency may be set or varied from sliceable composition, like, for example, Greek feta cheese, to a liquid.

Consistency, that is to say the firmness of the inventive material, however, may additionally be determined, in addition to the acid, also via the content of fat or the choice of fat; the amount and property of the fat then also serves for establishing firmness or consistency.

The acid or the acidulant to be added coagulates protein by pH reduction. This means that the maximum firmness can also be provided by a defined number of $H^+$ ions. The maximum firmness is at approximately a pH= 4.0, since, generally, no further setting occurs with further addition of acid above pH=4.0. Generally, however, below this value, the more acid is added, the higher the firmness that is reached. The pH should, however, be at most 5, since otherwise no further binding can be achieved.

For simpler adjustment of consistency, the following table may be prepared:

| higher sliceability | more liquid consistency |
|---|---|
| more acid | less acid |
| more fat | less fat |
| less water | more water |

However, an emulsion is only formed in a pH range <5, that is to say a minimum addition of acid may be necessary in order to ensure this range.

Further preferred exemplary embodiments are specified below.

In this case, the water content must be in the range from 45% to 25%, since otherwise no emulsion may be established.

The content of added fat is to be between about 30% and 50%.

A particularly preferred embodiment comprises:

| sunflower seed content about | 20% by weight |
|---|---|
| liquid | 54% by weight |
| preferably consisting of added water | 47% by weight and |
| lemon juice at about | 7% by weight |
| added fat | 26% |

The liquid variant can, by way of example, also be formulated by the preferred ratios.

Sunflower seed: added aqueous liquid: added fats or oils in the ratio of 3:8:4 at a pH=4.5.

The firmest variant can by way of example also be specified by the preferred ratios as follows:

sunflower seed: added aqueous liquid: added fats or oils in the ratio of 3:4:8 and pH=4.

The experience with inventive milk substitute teaches that the emulsion can be made up to be more solid or more liquid under the abovementioned limits. The emulsification process must be complete, since this product can then be extended to form milk with water or aqueous liquid.

Seeds which are preferred, but without restricting generality, are sunflower seeds, almonds, hazelnuts, walnuts, in single varieties and any mixtures of these.

Oils and fats which are preferred, but without restricting generality, are avocado oil, thistle oil, rapeseed oil, sunflower oil, almond oil, soybean oil, pumpkin seed oil, in each case in single varieties or in any mixing ratios.

Where percentages are given hereinafter, these are to be understood as percentages by weight in each case.

An inventive base product which has been given the trade name Ibi by the applicant is also obtained using finely ground sunflower seeds (20%), water (33.3%), salt (0.7%), sunflower oil (40%), lemon juice (6%).

Water, sunflower oil and salt can be varied depending on the desired consistency. All ingredients are added in sequence and mixed or whipped together. Then the product is pasteurized.

The inventive food can be sweetened using all sweeteners: refined sugar, concentrated agavae juice, concentrated apple juice, honey.

Preferred contents: inventive base material Ibi, as described above, (85%), sweetener (15%).

Soap, Shampoo and Toothpaste are Obtained from Ibi as follows:

Mix together Ibi base material as described above and tea tree oil (1 drop per 10 g of Ibi base material), then pasteurize. As an abrasive for mechanical cleaning, the following substances are suitable, inter alia: salt, cereal bran. These substances are added as desired in each case. Tea tree oil is a natural preservative. The shelf life can be further improved by permitted and generally known preservatives.

Instead of sunflower oil for the Ibi base, that is to say the Ibi base material, the following oils are also suitable: avocado oil, almond oil, jojoba oil.

Ibi Milk

Mix Ibi base material as described above with water in a ratio of 2:7. A particularly preferred enhancement uses pure vanilla, cocoa, finely ground almonds (up to a maximum of 2%).

These exemplary embodiments demonstrate conclusively to those skilled in the art the broad and versatile usability of the inventive substance, but are not suitable for restricting the generality of the invention.

The invention thus makes a substantial, important and fundamental contribution to a life less polluted with chemical substances or genetically modified products.

Furthermore, persons with allergies can again participate in many joys of a normal life which have been barred from them to date by their disease, since the preparation of the inventive substances in each case using single varieties permits the exclusion of undesired allergens with the high safety required.

What is claimed is:

1. A process for producing a viscous edible substitute for animal protein or tofu containing food comprising the following steps:
   providing comminuted shelled seeds or nuts;
   providing a first liquid; and combining the seeds or nuts and the first liquid to make a first substance;
   adding oil or liquefied fat to the first substance to make a second substance;
   providing an acidic second liquid or an acidulant and mixing said comminuted shelled seeds or nuts, said first liquid, said oil or liquefied fat and said acidic second liquid or acidulant to obtain a base substance;
   wherein the ratio of seeds or nuts to the first liquid is about 100:50 to 100:1000, based on their parts by weight;
   wherein the ratio of said seeds or nuts plus said first liquid to said oil or liquefied fat is about 100:20 to 100:300, based on their parts by weight; and
   wherein said acidic second liquid or acidulant is added in sufficient quantities to obtain a pH value <5 of the base substance, thereby resulting in a firmer consistency of the base substance;
   wherein said base substance is pasteurized yielding said viscous edible product.

2. Process according to claim 1, characterized in that the added oil or fat is produced from seeds or nuts.

3. Process according to claim 1, characterized in that the seeds or nuts originate from a single plant species.

4. Process according to claim 3, characterized in that the seeds are sunflower seeds.

5. Process according to claim 1, characterized in that the first liquid comprises water, fruit juice or vegetable juice or is produced from plants or fungi.

6. Process according to claim 1, characterized in that the acidic second liquid is lemon juice.

7. Process according to claim 1, characterized in that the quantitative ratios of seeds or nuts to the first liquid to salt or sugar are about 100:50 to 1000:0 to 200, based on their parts by weight.

8. Process according to claim 1, characterized in that the quantitative ratio of the pulpy first substance to oil or liquefied fat is about 100:20 to 300, based on their parts by weight.

9. Process according to claim 1, characterized in that the quantitative ratio of the acidic second liquid to the liquid second substance is about 2 to 20:100, based on their parts by weight.

10. Food characterized by the product of the process according to one of the preceding claims.

11. Toiletry characterized by the product of the process according to claim 1.

12. Toiletry according to claim 11, further containing a perfuming substance in the form of herb or plant constituents.

13. Cleaning agent characterized by the product of the process of claim 1.

14. Cleaning agent according to claim 13, characterized in that the cleaning agent has a granular constituent of coarsely ground sunflower seeds or sunflower bran, cereals, meal, bran, sawdust, grated coconut, sand or lime constituents.

15. Process according to claim 1, characterized in that the consistency of the substance produced is able to be determined by the amount of the added acidic second liquid or the acidulant, respectively.

16. Process according to claim 1, characterized in that the second substance is acidified by bacteria.

17. Process according to claim 1, wherein a water content is in the range from 45% to 25%.

18. Process according to claim 1, wherein the quantitative ratio of the acidic second liquid to the second substance is about 2 to 20:100, based on their parts by weight.

19. Process for producing a substance, characterized in that
   a stirrable first substance is produced from the comminution of shelled seeds or nuts,
   with addition of a first liquid and,
   oil or liquefied fat is added to this stirrable first substance and thus a second substance is produced, an acidic second liquid or an acidulant is added to this second substance, as a result of which a firmer consistency is obtained,
wherein the quantitative ratio of the first substance to oil or liquefied fat is about 100:20 to 300, based on their parts by weight;
wherein the quantitative ratio of the acidic second liquid to the second substance is about 2 to 20:100, based on their parts by weight;
wherein the second substance has a pH value <5; and
wherein the water content is in the range from 45% to 25%.

20. A viscous edible product, comprising a mixture of:
comminuted shelled seeds or nuts;
a first liquid;
a first liquefied fat; and
an acidic second liquid or an acidulant,
wherein the ratio of seeds or nuts to the first liquid is about 100:50 to 100:1000, based on their parts by weight;
wherein the ratio of said seeds or nuts plus said first liquid to said oil or liquefied fat is about 100:20 to 100:300, based on their parts by weight; and
wherein the product is acidified to a pH value <5 for having a firmer consistency;
wherein the product is pasteurized; and
wherein the consistency of the product is similar to curd cheese or fresh cheese.

* * * * *